United States Patent
Smith

(10) Patent No.: US 6,537,205 B1
(45) Date of Patent: Mar. 25, 2003

(54) ENDOSCOPIC INSTRUMENT SYSTEM HAVING REDUCED BACKLASH CONTROL WIRE ACTION

(75) Inventor: Kevin W. Smith, Coral Gables, FL (US)

(73) Assignee: SciMed Life Systems, Inc., Maple Grove, MN (US)

(*) Notice: Subject to any disclaimer, the term of this patent is extended or adjusted under 35 U.S.C. 154(b) by 27 days.

(21) Appl. No.: 09/716,710

(22) Filed: Nov. 20, 2000

Related U.S. Application Data

(63) Continuation-in-part of application No. 09/418,246, filed on Oct. 14, 1999.

(51) Int. Cl.[7] .................................................. A61B 1/00
(52) U.S. Cl. ........................ 600/104; 600/130; 600/140
(58) Field of Search ................................. 600/130, 104, 600/105, 106, 107, 140, 153; 606/205, 167

(56) References Cited

U.S. PATENT DOCUMENTS

| | | | |
|---|---|---|---|
| 1,127,948 A | 2/1915 | Wappler | |
| 3,805,770 A | * 4/1974 | Okada | ........................... 128/4 |
| 3,895,636 A | 7/1975 | Schmidt | ..................... 128/305 |
| 3,955,578 A | 5/1976 | Chamness et al. | ..... 128/303.15 |
| 4,256,113 A | 3/1981 | Chamness | ............. 128/303.14 |
| 4,294,254 A | 10/1981 | Chamness | ............. 128/303.14 |
| 4,326,530 A | 4/1982 | Fleury, Jr. | .............. 128/303.14 |
| 4,327,711 A | 5/1982 | Tagaki | ............................ 128/4 |
| 4,345,599 A | 8/1982 | McCarrell | ................... 128/320 |

(List continued on next page.)

FOREIGN PATENT DOCUMENTS

| | | |
|---|---|---|
| DE | 36 16 193 A1 | 11/1986 |
| DE | 94 18 834.3 U | 3/1995 |
| WO | WO 00/42926 | 7/2000 |
| WO | WO 00/53107 | 9/2000 |

OTHER PUBLICATIONS

U.S. patent application Ser. No. 09/716,776, Kevin W. Smith, filed Nov. 20, 2000.
Product Brochure, "Trio 14, Re–engineering Over–the–Wire Balloon Technology," 1994, 4 pages.

*Primary Examiner*—Linda C. M. Dvorak
*Assistant Examiner*—Jocelyn Ram
(74) *Attorney, Agent, or Firm*—Crompton, Seager & Tufte, LLC

(57) ABSTRACT

An endoscopic instrument has a control member, a portion of the member having an outer surface with a non-circular cross-sectional shape. The non-circular cross-sectional shape may be provided to the control member by providing peripheral projections or fins along the length of the portion or by providing the periphery of the portion with a polygonal shape. Where fins are used, the fins are preferably quite small and only have a minimal effect on the fluid flow cross-sectional area between the interior of the endoscope instrument shaft and the central control member. The resulting instrument has significantly reduced backlash in end effector assembly manipulation, while maintaining adequate fluid flow in the endoscope shaft. According to a second embodiment of the invention, a portion of the interior of the shaft of the endoscopic instrument has an interior surface having a non-circular cross-sectional shape by the inclusion of a plurality of radially spaced and inwardly directed ribs or by being polygonally shaped. The resulting endoscopic instrument likewise reduces the backlash experienced in operating the distal end effector assembly.

24 Claims, 4 Drawing Sheets

U.S. PATENT DOCUMENTS

| | | | |
|---|---|---|---|
| 4,430,083 A | 2/1984 | Ganz et al. | 604/283 |
| 4,493,320 A | 1/1985 | Treat | 128/303.15 |
| 4,590,938 A | 5/1986 | Segura et al. | 128/328 |
| 4,593,680 A | 6/1986 | Kubokawa | 128/4 |
| 4,619,260 A | 10/1986 | Magill et al. | 128/309 |
| 4,632,110 A | 12/1986 | Sanagi | 128/303 R |
| 4,706,656 A * | 11/1987 | Kuboto | 600/153 |
| 4,742,817 A | 5/1988 | Kawashima et al. | |
| 4,763,668 A | 8/1988 | Macek et al. | 128/751 |
| 4,785,825 A | 11/1988 | Romaniuk et al. | 128/751 |
| 4,790,831 A | 12/1988 | Skribiski | 604/282 |
| D301,614 S | 6/1989 | Kozak et al. | D24/30 |
| 4,840,176 A | 6/1989 | Ohno | 128/303.14 |
| 4,840,623 A | 6/1989 | Quackenbush | 604/280 |
| 4,869,238 A | 9/1989 | Opie et al. | 128/6 |
| 4,872,456 A | 10/1989 | Hasson | 128/321 |
| 4,905,691 A | 3/1990 | Rydell | 606/47 |
| 4,945,920 A | 8/1990 | Clossick | 128/751 |
| 4,950,232 A | 8/1990 | Ruzicka et al. | 604/43 |
| 4,967,732 A | 11/1990 | Inoue | 128/4 |
| 4,973,321 A | 11/1990 | Michelson | 604/280 |
| 5,005,755 A | 4/1991 | Takahashi et al. | 228/126 |
| 5,026,371 A | 6/1991 | Rydell et al. | 606/47 |
| 5,066,295 A | 11/1991 | Kozak et al. | 606/47 |
| 5,084,054 A | 1/1992 | Bencini et al. | 606/113 |
| 5,125,909 A | 6/1992 | Heimberger | 604/264 |
| 5,147,316 A | 9/1992 | Castillenti | 604/164 |
| 5,147,373 A | 9/1992 | Ferzli | 606/144 |
| RE34,110 E | 10/1992 | Opie et al. | 128/6 |
| 5,156,590 A * | 10/1992 | Vilmar | 600/105 |
| 5,158,561 A | 10/1992 | Rydell et al. | 606/113 |
| 5,163,942 A | 11/1992 | Rydell | 606/113 |
| 5,176,702 A | 1/1993 | Bales et al. | 606/208 |
| 5,179,935 A | 1/1993 | Miyagi | 128/4 |
| 5,183,470 A | 2/1993 | Wetterman | 604/281 |
| 5,201,740 A | 4/1993 | Nakao et al. | 606/113 |
| 5,201,743 A | 4/1993 | Haber et al. | 606/147 |
| 5,244,619 A | 9/1993 | Burnham | 264/173 |
| 5,254,117 A | 10/1993 | Rigby et al. | 606/46 |
| 5,254,130 A | 10/1993 | Poncet et al. | 606/206 |
| 5,279,280 A * | 1/1994 | Bacich et al. | 600/104 |
| 5,281,220 A | 1/1994 | Blake, III | 606/46 |
| 5,281,230 A | 1/1994 | Heidmueller | 606/127 |
| 5,290,294 A | 3/1994 | Cox et al. | 606/108 |
| 5,318,564 A | 6/1994 | Eggers | 606/47 |
| 5,334,169 A | 8/1994 | Brown et al. | 604/282 |
| 5,336,227 A | 8/1994 | Nakao et al. | 606/114 |
| 5,358,493 A | 10/1994 | Schweich, Jr. | 604/264 |
| 5,376,094 A | 12/1994 | Kline | 606/113 |
| 5,404,887 A * | 4/1995 | Prather | 600/434 |
| 5,406,939 A | 4/1995 | Bala | 128/4 |
| 5,439,478 A | 8/1995 | Palmer | 606/205 |
| 5,465,710 A | 11/1995 | Miyagi | 600/139 |
| 5,486,182 A | 1/1996 | Nakao et al. | 606/114 |
| 5,496,292 A | 3/1996 | Burnham | 604/282 |
| 5,501,692 A | 3/1996 | Riza | 606/148 |
| 5,542,948 A | 8/1996 | Weaver et al. | 606/113 |
| 5,591,202 A | 1/1997 | Slater et al. | 606/205 |
| 5,601,533 A | 2/1997 | Hancke et al. | 604/164 |
| 5,607,404 A * | 3/1997 | Khairkhahan | 604/264 |
| 5,647,846 A | 7/1997 | Berg et al. | 604/493 |
| 5,681,296 A | 10/1997 | Ishida | 604/282 |
| 5,685,822 A | 11/1997 | Harhen | |
| 5,685,853 A | 11/1997 | Bonnet | |
| 5,718,360 A | 2/1998 | Green et al. | 227/179 |
| 5,741,271 A | 4/1998 | Nakao et al. | 606/114 |
| 5,746,747 A | 5/1998 | McKeating | 606/144 |
| 5,755,724 A | 5/1998 | Yoon | 606/114 |
| 5,759,187 A | 6/1998 | Nakao et al. | 606/114 |
| 5,762,631 A | 6/1998 | Klein | 604/171 |
| 5,766,217 A | 6/1998 | Christy | 606/148 |
| 5,792,116 A * | 8/1998 | Berg et al. | 600/585 |
| 5,800,444 A | 9/1998 | Ridinger et al. | 606/113 |
| 5,814,052 A | 9/1998 | Nakao et al. | 606/115 |
| 5,817,111 A | 10/1998 | Riza | 606/148 |
| 5,820,464 A | 10/1998 | Parlato | 464/58 |
| 5,820,546 A * | 10/1998 | Ouchi | 600/104 |
| 5,827,177 A | 10/1998 | Omeda et al. | 600/121 |
| 5,846,248 A | 12/1998 | Chu et al. | 606/114 |
| 5,860,975 A | 1/1999 | Goble et al. | 606/45 |
| 5,882,347 A | 3/1999 | Mouris-Laan | 604/280 |
| 5,885,508 A | 3/1999 | Ishida | 264/313 |
| 5,906,620 A | 5/1999 | Nakao et al. | 606/113 |
| 5,906,621 A | 5/1999 | Secrest et al. | 606/114 |
| 5,957,932 A | 9/1999 | Bates et al. | 606/127 |
| 5,984,904 A | 11/1999 | Steen et al. | 604/264 |
| 5,984,920 A | 11/1999 | Steinbach | 606/47 |
| 5,993,474 A | 11/1999 | Ouchi | 606/206 |
| 6,001,096 A | 12/1999 | Bissinger et al. | 606/50 |
| 6,010,512 A | 1/2000 | Chu et al. | 606/113 |
| 6,015,381 A | 1/2000 | Ouchi | 600/104 |
| 6,015,415 A | 1/2000 | Avellanet | 606/113 |
| 6,024,708 A | 2/2000 | Bales et al. | 600/564 |
| 6,050,995 A | 4/2000 | Durgin | 606/47 |
| 6,068,603 A | 5/2000 | Suzuki | 600/565 |
| 6,071,233 A | 6/2000 | Ishikawa et al. | 600/104 |
| 6,074,408 A | 6/2000 | Freeman | 606/205 |
| 6,090,073 A | 7/2000 | Gill | 604/164 |
| 6,090,129 A | 7/2000 | Ouchi | 606/206 |
| 6,093,195 A | 7/2000 | Ouchi | 606/113 |

* cited by examiner

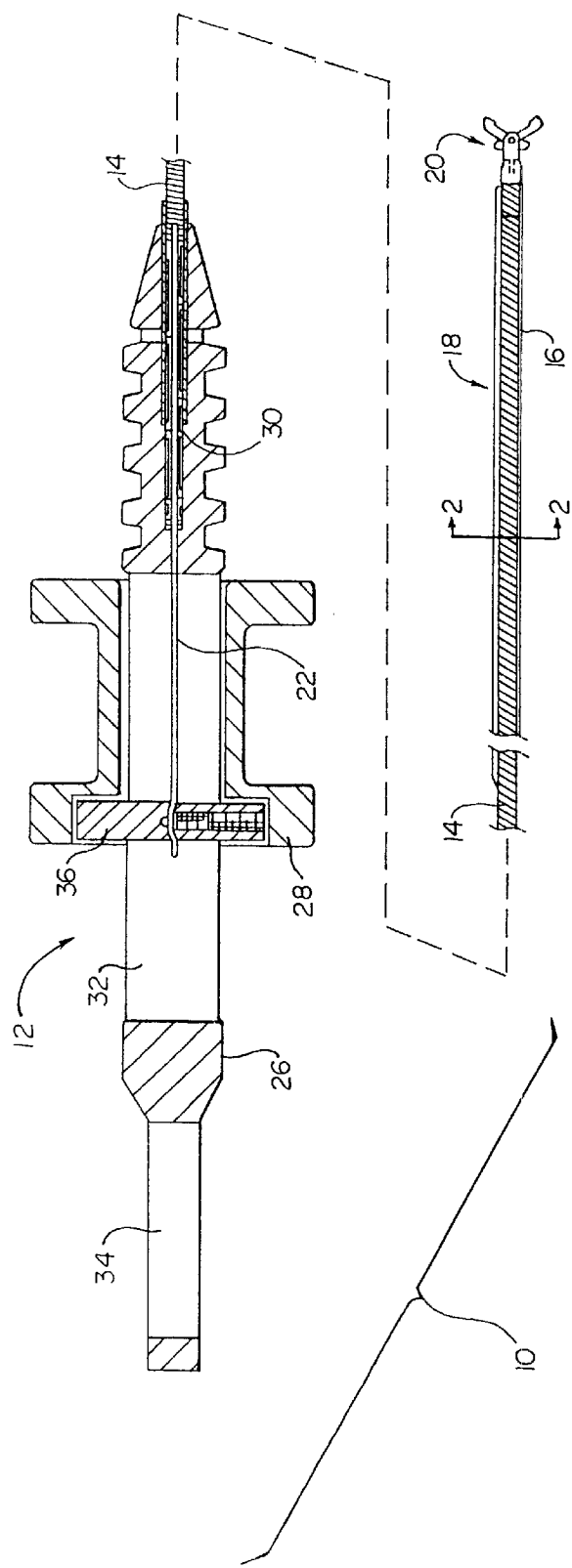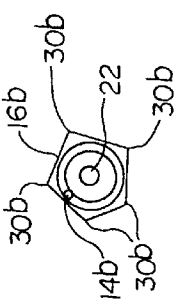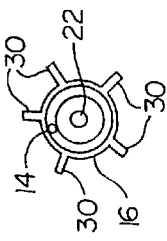

ENDOSCOPIC INSTRUMENT SYSTEM HAVING REDUCED BACKLASH CONTROL WIRE ACTION

CROSS REFERENCE TO RELATED APPLICATIONS

This application is a continuation-in-part of U.S. patent application Ser. No. 09/418,246, filed on Oct. 14, 1999, entitled "Endoscope and Endoscopic Instrument System Having Reduced Backlash When Moving The Endoscopic Instrument Within A Working Channel Of The Endoscope," the entire disclosure of which is hereby incorporated by reference.

FIELD OF THE INVENTION

This invention relates broadly to surgical instruments. More particularly, this invention relates to an endoscope and endoscopic surgical instruments adapted to be extended into a channel of the endoscope.

BACKGROUND OF THE INVENTION

At the present time there are many instruments made for use in endoscopic medical procedures. Typically, endoscopic instruments are long and flexible cylindrically tubular devices with manually operated handles at their proximal ends and tissue-manipulative cutting, grasping, injecting, or cauterizing components at their distal ends. These distal devices, also called effector-end assemblies, after being moved to the intended treatment site by means of the endoscopic instrument tube, are operated by a control member, such as a wire. The control member typically may be pushed as well as pulled, to allow motion of the control element, and therefore operation of the distal device, in both directions. For example, the control member may allow a physician to close and open a pair a forceps by moving one of the forceps jaws relative to the other, which may be fixed. Alternatively, a biopsy or other needle may penetrate tissue by being inserted into such tissue at the distal end of the endoscopic instrument tube by pushing the control member distally by means of the control member's proximal handle. Further, a snare may be included as the effector-end assembly as disclosed in commonly assigned U.S. patent application Ser. No. 09/716,600, entitled Polypectomy Snare Having Ability to Actuate Through Tortuous Path," filed on the same day herewith, the disclosure of which is hereby incorporated by reference.

The endoscopic instruments are introduced into a flexible endoscope which is inserted into the patient through a natural or surgically-created opening. The endoscope includes an elongate portion defining several lumens therethrough and a proximal handle for directing the elongate portion. At least one lumen is provided with an optical imaging system (e.g., a scope), and several lumina or "working channels" are typically provided for extending endoscopic instruments therethrough. The working channel of the endoscope typically consists of a PTFE-lined cylindrical tube passing from the proximal (handle) end of the endoscope to its distal (working) end. Working channels are typically 2 to 4 millimeters in inside diameter.

During the medical procedure, the doctor passes one or more endoscopic instruments through the working channel or channels in order to manipulate the tissue being visualized by the optical system of the endoscope. In the course of positioning the distal effector end assembly, usually the doctor must repeatedly manipulate the distal end of the instrument by manually pushing and pulling on the proximal portion of the tubular shaft of the endoscopic instrument near where the shaft enters the handle of the endoscope. After the end effector assembly has been placed at the treatment site, the end effector assembly must similarly be manipulated or effected using the control element. For example, the physician may wish to open or close a forceps, or insert a needle into tissue at the distal end of the endoscopic instrument and then withdraw the needle without moving the entire tubular shaft of the needle instrument.

The view through an endoscope is highly magnified when seen on the video monitors typically used for these procedures; a field of view that may be a few millimeters across would be enlarged to several inches on the video screen. Accordingly, the instrument must be moved very precisely in very small increments in order to approximate and treat the tissue being visualized. In fact, many times, the doctor must position the distal tip of the endoscopic instrument within a fraction of a millimeter of the desired location in order to achieve desired results. However, because of friction and backlash in the way the instrument passes through the endoscope, achieving this level of accuracy is difficult. For example, an endoscope several feet long may be positioned in the colon of a patient with the distal end of the endoscope tightly reflexed to visualize a particular area of the ascending colon. In such a position, the endoscope is bent into a very sinuous shape in multiple planes. Since the outside diameter of the endoscopic instrument is significantly smaller (e.g., 2.2 mm) than the inside diameter of the working channel (e.g., 3.2 mm), a large clearance space exists between the instrument and the channel. Likewise, there is a discrepancy between the outside diameter of the control member in comparison with the inside diameter of the endoscopic instrument tubular shaft. The outside diameter of a control member may be as small as 1 mm, while the inside diameter of the endoscopic instrument outer tube may be approximately 2 mm.

When the instrument is pulled back, the tension on the instrument causes the instrument to be pulled taut, and the instrument naturally assumes the shortest path through the working channel. When the instrument is pushed forward, friction causes it to assume the longest path through the channel (that is, the shaft of the instrument must "fill" the working channel before the distal end of the instrument begins to move). As a result, quite a bit of backlash (lost motion) is experienced by the doctor when the doctor tries to manipulate the distal end of the instrument. If it is necessary to pull the tip back a bit, the backlash must first be pulled out before the distal end can be retracted. If the doctor pulls the instrument back a little too far, the doctor must then push it several millimeters forward before there is any motion at all at the distal end. During this manipulation, the endoscopic instrument alternately assumes the longest-path and shortest-path positions within the working channel of the endoscope.

The situation with regard to the control member is analogous. As the control member is moved distally and proximately vis-à-vis the outer tube of the endoscopic instrument, the control member is respectively forced to fill the instrument tube, or be pulled taut, before the desired movement of the end effector assembly takes place. In both the movement of the endoscopic instrument through the working channel and the movement of the control member within the endoscopic instrument tube to operate the end effector assembly, it is desirable to minimize lag, or backlash. If this backlash can be reduced or eliminated, the manipulation of the distal end of the endoscopic instrument as a whole, or the operation of the device at the distal end of the endoscopic instrument operated by the control member, can be made much easier and more responsive, and the doctor can achieve his desired positioning or device operation more easily, rapidly, and precisely. In particular, a reduction in the backlash experienced in operating the end effector assembly with the control member would increase the precision of surgical techniques possible with the endoscopic instrument. However, this is not a simple problem to overcome for several reasons.

The backlash situations described above could possibly be reduced or substantially eliminated if the clearance between the outside of the control member and the inside of the tubular shaft of the endoscopic instrument were reduced. However, this is not a practical solution, because it is often necessary to inject fluid (or to operate suction) through the annular space between these two structures. If the control member were to substantially fill up the space within the tubular casing, the backlash would be reduced, but there would be greatly reduced ability to conduct fluid through the working channel around the instrument. In fact, because of the nature of fluid flow, as the aspect ratio of the annular clearance space (the ratio of the thickness of the fluid channel to its circumferential length) becomes small, the impedance to fluid flow grows disproportionately to the reduction in cross-sectional area of the fluid passage.

In addition, as the diameter of the control member approaches the inside diameter of the tubular casing, the area of contact between the instrument and the working channel becomes larger. This increase in contact area between these parts results in an increase in frictional drag on the control member when the doctor attempts to move it relative to the tubular shaft.

SUMMARY OF THE INVENTION

The present invention provides an endoscopic system with little or no backlash, or lag, when manipulating an outer tube of an endoscopic instrument relative to an endoscope working channel and/or a control member of the instrument relative to the outer tube containing such control member, while maintaining an open area therebetween for permitting fluid flow and/or relative movement without excessive friction.

An endoscopic system is provided where either a portion of the endoscopic instrument shaft or a portion of the control member is provided with a non-circular cross-section.

Generally, an endoscopic instrument includes an elongate flexible tubular member having proximal and distal ends, a control member having proximal and distal ends and extending through the tubular member, an end effector assembly coupled either to the distal end of the control member, or the distal end or both the control member and the distal end of the tubular member, and a handle means for moving the control member relative to the tubular member to operate the end effector assembly.

According to a first embodiment of the invention, at least a portion of the elongate control member of the endoscopic instrument has an outer surface having a non-circular cross-sectional shape. The non-circular cross-sectional shape may be provided to the portion of the control member by radially spacing a plurality of fins, ridges, lands, or other projections about the periphery (exterior) of the portion, or by providing the portion with a polygonal cross-sectional shape. Where fins or ridges are provided, they can be quite small and will only have a minimal effect on the fluid-flow cross-sectional area between the shaft of the endoscopic instrument and the control member. Thus, the resulting endoscopic instrument will have significantly reduced backlash in effector end assembly operation, while maintaining adequate fluid flow in the lumen of the tubular instrument shaft. In addition, the fins or corners of the polygonal shape provide few and relatively small contact points so that the control member may be easily moved within the lumen of an endoscope instrument shaft. The fins or ridges on the control member, or other non-circular outer shape, may be imparted by the use of a die during extrusion, the die having a shape complementary to that desired in the control member.

According to a second embodiment of the invention, an instrument, preferably designed for use via insertion in an endoscope working channel, is provided having a proximal handle, and an elongate flexible distal portion with an outer tubular shaft having a lumen therethrough, within which is a longitudinally extending control member. The outer tubular shaft, with the lumen therein along its length, includes a substantial portion wherein the inner lumen of the outer shaft has a non-circular cross-sectional shape. The non-circular cross-sectional shape can be provided to the lumen of the shaft by providing the interior surface of the shaft with a plurality of radially spaced and inwardly directed ribs or other projections, or by providing the interior surface of the instrument shaft with a polygonal shape. The ribs can be quite small and will only have a minimal effect on the fluid flow cross sectional area between the working channel and the endoscopic instrument. Therefore, the resulting endoscopic instrument will reduce the control member backlash of the endoscopic instrument while maintaining adequate fluid flow in the lumen of the endoscopic instrument shaft. Additionally, the control member will be easily moved to operate the distal effector end assembly, as there will be few and relatively small contact points between the two. The outer tubular shaft may also have a non-circular outer diameter cross-sectional slope in order to reduce backlash of the endoscopic instrument as a whole with a working channel.

Under a preferred embodiment of the present invention according to either alternative discussed above, the control member itself may have a lumen for the passage of fluid through the control member, particularly when the distal effector end assembly of the endoscopic instrument is a hollow or hypodermic needle. The control member may also have a central lumen whenever it may be desired to irrigate or provide suction through the control member in addition to any fluid flows effected through other parts of the endoscopic instrument, such as the tubular shaft and the endoscope working channel. Also in a preferred embodiment of the present invention, the outer surface of the endoscopic instrument's tubular shaft, or the inner surface of the endoscope working channel through which the instrument is introduced, has a non-circular cross-sectional shape in order to reduce backlash in the movement of the endoscopic instrument through the working channel, as described in U.S. patent application Ser. No. 09/418,246, filed on Oct. 14, 1999, entitled "Endoscope and Endoscopic Instrument System Having Reduced Backlash When Moving The Endoscopic Instrument Within A Working Channel Of The Endoscope," the entire disclosure of which is hereby incorporated by reference.

Additional objects and advantages of the invention will become apparent to those skilled in the art upon reference to the detailed description taken in conjunction with the provided figures.

BRIEF DESCRIPTION OF THE DRAWINGS

FIG. 1 is a longitudinal cross-sectional view of one embodiment of an endoscopic instrument of the present invention;

FIG. 2a is an enlarged cross-section across line 2—2 in FIG. 1, according to a first embodiment of the invention;

FIG. 2b is an enlarged cross-section across line 2—2 in FIG. 1, according to an alternative first embodiment of the invention;

DETAILED DESCRIPTION OF THE PREFERRED EMBODIMENTS

Figure 3:
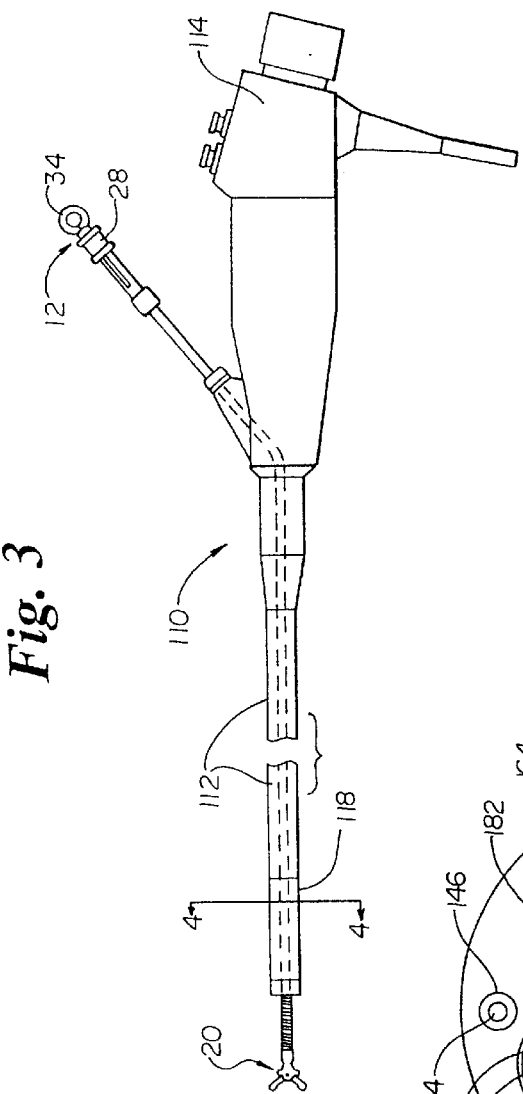
FIG. 3 is a side elevation of an endoscope according to the invention shown provided with an endoscopic instrument according to the invention.

Turning now to FIG. 1, an endoscopic instrument 10 for insertion through a working channel of an endoscope is shown. According to a first embodiment of the invention, the endoscopic instrument 10 includes an actuation handle 12, a tubular coil 14, a jacket 16 provided about at least a distal portion 18 of the coil 14, an end effector assembly 20, e.g., a biopsy forceps, and a control wire 22. The actuation handle 12 typically includes a stationary member 26 and a displaceable spool 28. The stationary member 26 includes a distal throughbore 30, a central slot 32, and a proximal thumb ring 34. The displaceable spool 28 is slidably disposed on the stationary member 26 and has a cross member 36 which passes through the slot 32. The proximal end of the control wire 22 is coupled to the spool 28. Operation of the actuation handle 12 is described fully in U.S. Pat. No. 5,228,451 to Bales, which is hereby incorporated by reference herein in its entirety. In brief, longitudinal movement of the spool 28 within the slot 32 results in operation of the end effector assembly 20 (i.e., the end effector assembly moves between open and closed positions).

Referring now to FIGS. 1 and 2a, in accord with the first embodiment of the invention, the jacket 16 is a low-friction coating or sheath, preferably made from PTFE, extending over at least a distal portion of the coil 14. The jacket 16 may be extruded over the portion of the coil, or may be provided as an attachment capable of being provided over an assembled endoscopic instrument. For example, the jacket may be a tubular member having a longitudinal slit. The jacket 16 defines several (e.g., five) longitudinal fins 30 radially spaced about the coil. By way of example, and not by limitation, for an endoscopic instrument intended to be inserted into an endoscope having a working channel of 3.2 mm inside diameter, the jacket 16 is preferably a cylinder 2.2 millimeters in diameter with thin fins (or lands) having a thickness of approximately 0.1 mm and extending approximately 0.4 mm out from the coil surface. Such a construction would almost completely fill the diameter of the working channel of the endoscope (i.e., the radial dimension of the jacket, from the center of the coil 14 out to the end of a fin 30) and is nearly equal to the radius of the working channel), substantially reducing the motion backlash. However, since the fins 30 are quite thin, only a small amount of the fluid-flow cross sectional area would be sacrificed. Additionally, the number of contact points and surface area of contact points between the fins and the interior of the working channel is minimal.

It is also preferable that the fins extend along only a distal portion of the endoscopic instrument rather than along the entire length of the endoscopic instrument. If the fins 30 were to extend to the most proximal portion of the coil 14, it would be difficult to effect a fluid seal against the shaft of the instrument where the coil enters the endoscope handle. Such a seal is needed if fluid is to be injected through the working channel. Since the majority of the flexing of the endoscope in an endoscopic procedure takes place at the distal portion, where the endoscope is situated inside the patient, the majority of motion backlash results from the looseness of the instrument in the distal portion of the endoscope. Accordingly, it is preferable for the fins 30 to be placed on only the corresponding distal portion 18 of the endoscopic instrument 10 (for example, on the distal 150 cm of a 240 cm instrument) while leaving the proximal portion (i.e., 90 cm) a smooth cylinder. Such an endoscopic instrument would then have greatly reduced motion backlash when manipulated by the physician, and it would allow substantially unimpeded fluid flow through the working channel of the endoscope, while providing an easily sealed-upon surface where the instrument exits the endoscope handle.

Turning now to FIG. 2b, according to an alternate first embodiment of the invention, the jacket 16b has a non-circular cross-sectional shape over the coil 14 such that the cross-sectional shape is generally polygonal. For example, the jacket 16b may have a pentagonal shape, as shown. By way of example, and not by limitation, for an endoscopic instrument intended to be inserted into an endoscope having a working channel of 3.2 mm inside diameter, the corners 30b of the polygon preferably extend approximately 0.4 mm from the coil surface. Such a construction substantially completely fills the diameter of the working channel of the endoscope, substantially reducing the motion backlash, yet only contacts the working channel at the corners 30b. In addition, space is provided between the sides of the jacket and the working channel for fluid-flow.

Figure 4:
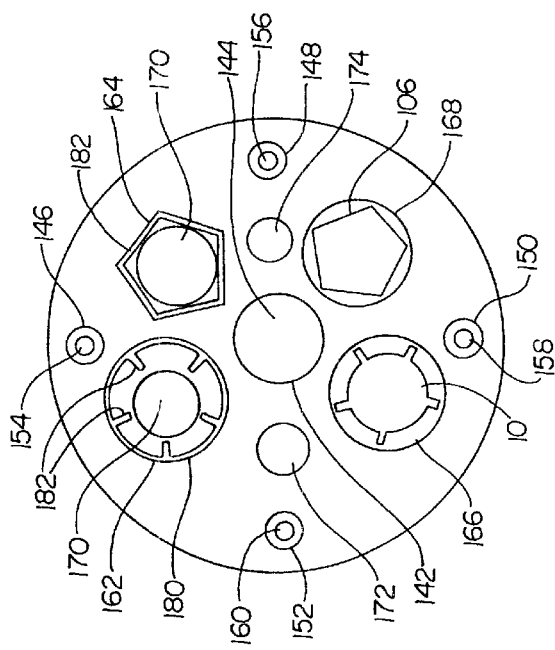
FIG. 4 is an enlarged cross-section across line 4—4 in FIG. 3, illustrating several working channel-endoscopic instrument systems according to the invention.

Referring now to FIGS. 3 and 4, an endoscope 110 according to a second embodiment of the invention is shown. The endoscope 110 includes an elongate tubular portion 112 and a proximal handle portion 114 adapted to manipulate and direct the distal end of the tubular portion 112. The tubular portion 112 has a plurality of lumens, with one lumen 142 provided for receiving an optical scope or camera device 144 (which may be built therein), several lumens 146, 148, 150, 152 provided for receiving control wires 154, 156, 158, 160 extending from the handle portion 114 through the tubular portion 112, and at least one, and preferably several, working channels 162, 164, 166, 168 for receiving endoscopic instruments 170 therethrough. For example, endoscopic instruments 10, 10b according to the first embodiment of the invention (as shown in FIGS. 2a and 2b, respectively) may be provided in working channels 166, 168. The working channels have proximal openings in the handle portion 114. Other lumens 172, 174 may be provided for other purposes. Endoscopes are described in general in U.S. Pat. No. 5,179,935 to Miyagi, which is hereby incorporated by reference herein in its entirety.

According to the second embodiment of the invention, a portion of at least one of the working channels 162 is provided with a non-circular cross-sectional shape. The non-circular cross-sectional shape may be molded into the working channel or more preferably is provided by a low-friction (e.g., PTFE) insert 180 preferably fixed within a distal portion 118 of the working channel 162. The insert 180 includes a plurality of radially spaced and radially inwardly directed longitudinal ribs 182. The ribs 182 can be quite small. For example, the ribs 182 may be approximately 0.1 mm thick and have a radial length of approximately 0.5 mm. Therefore, the ribs would have a minimal effect on the fluid flow cross-sectional area between the working channel and the endoscopic instrument, and also provide relatively small contact points between the working channel and the endoscopic instrument.

According to an alternate second embodiment of the invention, a working channel 164 is provided with a polygonal cross-sectional shape. The polygonal cross-sectional shape may be provided to the working channel 164 via an insert 182 or may be molded integrally into the working channel.

In each of the alternate embodiments, the working channel is adapted to provide reduced backlash, while maintaining adequate fluid flow in the working channel around the endoscopic instrument, and minimal contact between the endoscopic instrument and the working channel. In each alternate embodiment, the non-circular cross-sectional shape of the working channel may extend the entire length of the channel or a portion thereof.

There have been described and illustrated herein several embodiments of an endoscope and endoscopic instrument system having reduced backlash when moving the endoscopic instrument within the working channel of the endoscope. While particular embodiments of the invention have been described, it is not intended that the invention be limited thereto, as it is intended that the invention be as broad in scope as the art will allow, and that the specification be read likewise. Thus, while a particular biopsy forceps endoscopic instrument has been disclosed, it will be appreciated that endoscopic instruments having other end effectors, e.g., scissors, punches, needles, etc., can be provided with the non-circular cross-section of the invention, as well. Furthermore, while a PTFE has been disclosed for the jacket of the instruments and insert for the endoscope, other low friction materials can be used as well. Also, while a particular number of fins and ribs have been disclosed, it will be appreciated that other numbers of fins and ribs can be used. Alternatively, one or more spiral fins or ribs can be provided. Furthermore, projections other than fins can be used. Moreover, other polygonal shapes may be used for the jacket over the coil and the endoscope insert. Also, the coil and/or jacket may be substituted with another tubular member having a non-circular cross-section. For example, the tubular member may be extruded with a polygonal shape or with fins.

Figure 5:
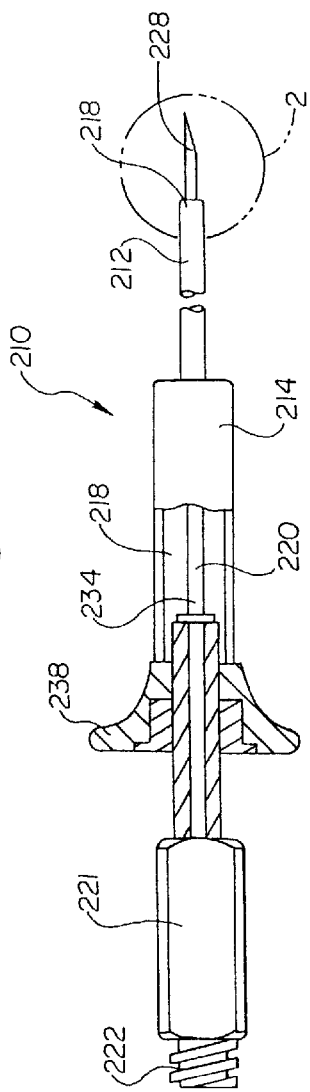
FIG. 5 is a plan view of an endoscopic injection instrument with reduced control member backlash according to one embodiment of the invention.

Referring now to FIG. 5, in accordance with an additional embodiment of the invention, an endoscopic instrument 210 is shown, which may be used in an endoscope such as endoscope 110 depicted in FIG. 3 and in axial cross-section in FIG. 4. For example, endoscopic instrument 210 may occupy the position of endoscopic instruments 10, 170, or 106 within working channels 162, 164, 166, or 168 in FIG. 4. The endoscopic instrument 210 includes an elongate tubular shaft 212 and a proximal handle portion 214 adapted to manipulate and direct the distal end of the tubular portion 212. The tubular portion 212 has a lumen 218 provided for receiving a control member 220 (which may be built therein) and which may be tubular, having a central lumen, if dictated by the design of the distal effector end assembly at the distal end of the control member. The endoscope instrument 210 of FIG. 5, an injection needle instrument, may be advanced through the working channel of an endoscope in substantially the same manner as endoscopic instrument 10 of FIG. 1, a forceps device. Alternatively, a snare may be incorporated as the distal effector end assembly.

The endoscopic needle 210 may also have ridges or fins along the outer shaft 212, or the outer wall of the shaft may otherwise have a non-circular cross-sectional shape, as shown with device 10 in cross-sections in FIGS. 2a and 2b and devices 10 and 10b of FIG. 4. The embodiment depicted in FIGS. 7–10, however, has a substantially circular outer cross-section. Furthermore, while endoscopic forceps 10 contains as part of its shaft a wound coil 14, or 14b in FIG. 2b, endoscopic needle 210 may or may not have a wound coil member making up part of its outer shaft. Endoscopic needle 210, as depicted in FIGS. 5–11, has no wound coil in its outer shaft 212.

Endoscopic needle device 210 has an elongate shaft 212 which is long enough to be advanced through endoscope working channels 162, 164, 166, or 168 of FIG. 4 so that proximal shaft handle 214 and proximal actuation member handle 221 remain outside of the endoscope working channel, similar to the position of the proximal handle and actuation handle 216 of endoscope forceps 10, as shown in FIG. 3. Returning to FIG. 5, tubular shaft 212 of endoscope needle 210 is made sufficiently long so that while proximal handles 214 and 221 project out of the proximal end of a working channel such as 162, 164, 166, or 168 in FIG. 4, at least distal end 218 of tubular shaft 212 will reach to the distal end of the respective working channel at the distal end of the endoscope. In a representative embodiment of the present invention, tubular shaft 212 is approximately 200 cm long. Within tubular shaft 212, inner control member 220 is joined at its proximal end to proximal actuation handle 221. Actuation handle 221 has at its proximal end a fitting 222 for attachment of a fluid or suction source. In a preferred embodiment, this fitting 222 is a standardized fitting such as a luer fitting.

Figure 6:
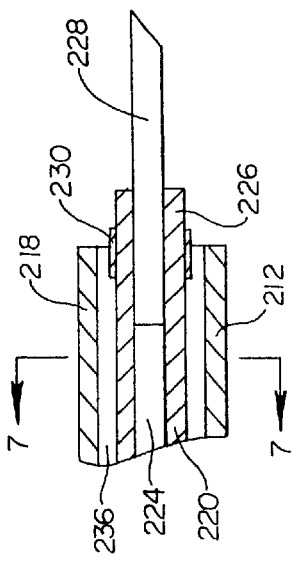
FIG. 6 is a cross-sectional view of the distal end of the instrument shown in FIG. 5.

The distal end 218 of the tubular shaft 212 and of inner control member 220 is shown in a detailed longitudinal cross-section in FIG. 6. In a representative embodiment of the present invention, inner control member 220 is tubular and has a central lumen 224. The central lumen 224 extends throughout inner control member 220, thereby allowing fluid communication throughout control member 220, to provide a path for fluid delivery to or suction from the distal end 226 of tubular control member 220. At the distal end 226 of inner control member 220, a hollow needle 228 is fitted within the inner control member. In a preferred embodiment, the hollow needle 228 has an outer diameter equal to or slightly larger than the inner diameter of control member 220 prior to placement of needle 228 within inner control member lumen 224. To secure needle 228 within control member lumen 224, a crimp sleeve 230 is preferably placed around the distal end 226 of control member 226 and crimped tightly around the tubular control member 220. In a preferred embodiment of the device, a shrink tube or painted band, not depicted, surrounds the tubular shaft of the device toward the distal tip 218 to aid in visibility of the distal end 218 of the device 210. For example, if the control member 220 and tubular shaft 212 are translucent or clear, a colored band may surround the tubular shaft 212 at its distal end 218. If the endoscopic instrument 210 is to be used in a radiographic procedure, the entire device may be opaque, for example, black. In the radiography use of the device 210, the crimp tube 230 which secures needle 228 may provide a radiopaque marker of the distal end 218 of the instrument 210 in general, and of the needle 228 in particular.

Figure 7:
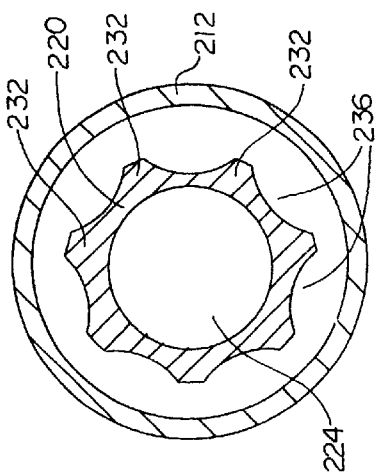
FIG. 7 is a radial cross-sectional view of the tubular shaft of the endoscopic instrument of FIG. 6, across line 7—7.

A radial cross-section of a representative embodiment of the shaft 212 and control member 220 of endoscope needle device 210 of FIG. 5 is depicted in FIG. 7. The outer shaft 212 is depicted with a substantially circular outer and inner cross-sectional shape, although, as previously discussed, the outer surface of tubular shaft 212 may have a non-circular cross-sectional shape in order to reduce backlash between the endoscopic instrument tubular shaft 220 and a smooth working channel of the endoscope, such as working channel 166 or 168 in FIG. 4. Within tubular shaft 212, the cross-sectional shape of tubular control member 220 is shown to have a number of longitudinal ridge-like projections 232 radiating from the central axis of the control member lumen. In a preferred embodiment, these projections 232 increase the effective outer diameter of control member 220 to be almost equal to or equal to the inner diameter of tubular shaft 220, thus reducing backlash of the control member vis-à-vis the tubular shaft, much in the same way that backlash may be reduced between the tubular shaft 212 and working channel 166 or 168, as previously discussed. For clarity of illustration, the ridge-like longitudinal projections 232 are depicted as not touching the inner wall of the tubular shaft 212, but in a preferred embodiment, preferably a majority of the ridges will contact the inner wall of tubular shaft 212 in order to better prevent device actuation backlash.

The longitudinal ridges 232 in the outer surface of the control member 220 may be formed by a process of extrusion through a die that is complementary to the desired cross-sectional shape of the tubular shaft 220 of FIG. 7. Other methods of creating the ridge projections 232 in control member 220 are possible, including the imparting of ridges 232 by means of a jacket surrounding a central tubular control element such as a hypotube or another tubular material. By way of example, and not by limitation, for an endoscopic instrument intended to be inserted into an endoscope having a working channel lumen of 3.2 mm inside diameter, the tubular shaft 212 of the endoscopic instrument may have a maximum outer diameter of approximately 2.2 mm and an inner diameter of about 1.8 mm. In such a device, the control member is preferably a member with a circular cross-section 1.2 millimeters in diameter with thin ridges (or lands) extending approximately 0.2 mm out from the control member's general outer diameter surface. Such a construction would almost completely fill the inner diameter of the instrument shaft of the endoscope (i.e., the radial dimension of the tubular control member 220, or tubular core of control member 220 together with ridges 232, from the center of the lumen 224 out to the end of a ridge 232, is nearly equal to the radius of the shaft 212 inner lumen), substantially reducing the motion backlash experienced by the operator in effecting the device end effector assembly. However, the ridges 232 still permit fluid flow in the remaining spaces 236 outside of the tubular control member 220. Additionally, the number of contact points and surface area of friction creating contact points between the fins 232 and the interior of the outer shaft 212 is minimal.

In an alternative embodiment, the ridges may extend along only a distal portion of the control member, rather than along the entire length of the control member. If the ridges 232 were to extend to the most proximal portion 234 of the control member 220, and fluid flow is being effected through the lumen 236 between control member 220 and outer tubular shaft 212, it may, in some embodiments, complicate the creation of a fluid seal against the device handle 238 where the control member 220 interfaces with the control member's proximal handle 238. Such seal is not needed, however, if the only fluid flow to be effected is injection or suction through the lumen 224 of control member 220, for example, where the distal effector assembly 228 is a hypodermic or other hollow needle as depicted in FIGS. 5 and 6. Since the majority of the flexing of the endoscope in an endoscopic procedure takes place at the distal portion, where the endoscope is situated inside the patient, the majority of motion backlash results from the looseness of the control member 220 in the distal portion of the endoscope tubular shaft 212. Accordingly, backlash in end effector assembly operation will still be substantially reduced even if the ridges 232 are placed on only the corresponding distal portion of the control member 220 (for example, on the distal 25–50 cm of a 200 cm instrument) while leaving the proximal portion (i.e., 150–175 cm) a smooth cylinder. Such a control member would then have greatly reduced motion backlash when the end effector assembly is manipulated by the physician, and it would allow substantially unimpeded fluid flow through the tubular shaft lumen 236, while providing a more easily sealed-upon surface where the control member exits the tubular shaft proximal handle 238. In the alternative, if the entire length of the control member 220 is ridged, for example, by extrusion through a complementary die, a fluid seal may still be accomplished by the use of a crimp sleeve binding the control member tube around a hypotube or similar smooth and relatively rigid tube inserted into the lumen of the control member tube in the area of tubular shaft handle 238.

If the tubular shaft of the endoscopic instrument 210 is generally smooth, as depicted in FIGS. 7–10, reduction of backlash in movement of the tubular shaft vis-à-vis the working channel may be effected by imparting to a working channel a non-circular lumen shape, as previously discussed with reference to working channels 162 and 164 of FIG. 4. For example, the working channel of the endoscope may be supplied with an insert having a non-circular cross-section, such as insert 180 inserted into working channel 162.

Figure 8:
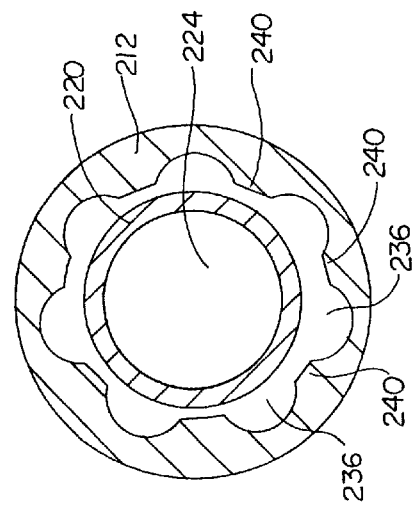
FIG. 8 is a radial cross-sectional view of the tubular shaft of the endoscopic instrument of FIG. 6 across line 7—7, according to an alternate embodiment of the present invention.

Referring now to FIG. 8, an alternate radial cross-section along line 7—7 of FIG. 6, depicting an alternate embodiment of the invention, is shown. FIG. 8 depicts a cross-sectional view of the distal end of the endoscopic device in which a non-circular cross-sectional shape is imparted to the inner surface of tubular shaft member 212 in order to reduce backlash in movement of circular shaped control member 220 during end effector assembly operation. The non-circular shape of tubular shaft member 212 may be imparted by compression with heat shrink tubing over an appropriately textured mandrel.

The application of heat to the tubular shaft will impress the desired ridges into the lumen of the tubular shaft. Alternatively, to impart ridges into the lumen of the tubular shaft, the tubular shaft may be formed by extrusion of the desired tubular shape using a complementary die through which the material of the tubular shaft is extruded. The tubular shaft may be extruded from a low friction material.

The ridges 240 can be quite small. For example, the ridges 240 may be approximately 0.2 mm thick and have a radial length of approximately 0.2 mm. Therefore, the ridges would have a minimal effect on the fluid flow cross-sectional area between the working channel and the endoscopic instrument, and also provide relatively small contact points between the working channel and the endoscopic instrument.

Figure 9:
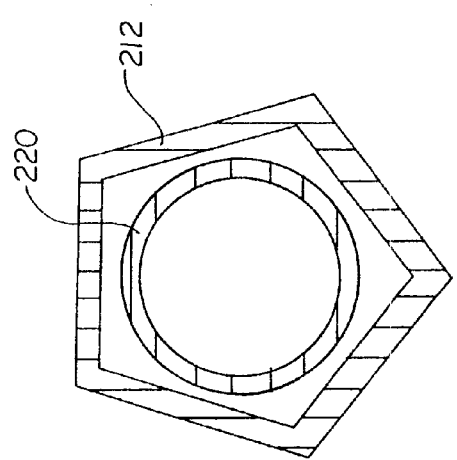
FIG. 9 is a radial cross-sectional view of the tubular shaft of the endoscopic instrument of FIG. 6 across line 7—7, according to an alternate embodiment of the present invention.
Figure 10:
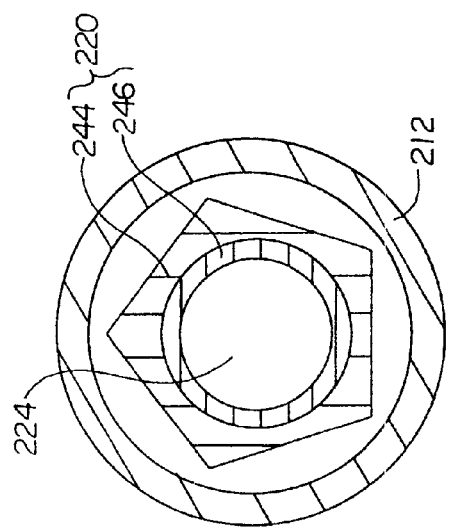
FIG. 10 is a radial cross-sectional view of the tubular shaft of the endoscopic instrument of FIG. 6 across line 7—7, according to an alternate embodiment of the present invention.

FIG. 9 shows a cross-section along line 7—7 of FIG. 6 of an alternate embodiment with a control member having a non-circular outer wall and inner wall. This formation of the control member may be compared to the endoscopic device depicted in cross-section in FIG. 2b, or to endoscopic device 108 in FIG. 4, in which an endoscopic shaft with a polygonal cross-sectional shape is disposed within a working channel with a substantially circular cross-sectional shape. For the polygonal cross-section tubular control member, by way of example and not by limitation, for a control member 220 intended to be in an endoscopic instrument shaft 212 having a lumen of 1.8 mm inside diameter, the corners 242 of a five-cornered polygon, or pentagon, preferably extend approximately 0.8 mm from the center of the control member lumen 224. Such a construction substantially completely fills the diameter of the endoscope shaft lumen, substantially reducing the end effector assembly actuation backlash, yet only contacts the working channel at the corners 242, analogous to the relationship between polygonal endoscopic device shaft 106 and working channel 168 in FIG. 4. In addition, space 236 is provided between the sides of the control member 220 and the instrument shaft 212 lumen for fluid flow, in the same way as space is provided in working channel 168 in FIG. 4. Other embodiments are possible, as depicted in FIG. 10, including a control member 220 having a non-circular outer wall, with an inner wall having a substantially circular cross-sectional shape. For example, a polymeric jacket 244 may be placed over a hypotube core 246 to provide a control member 220 having a non-circular cross-sectional shape.

Figure 11:
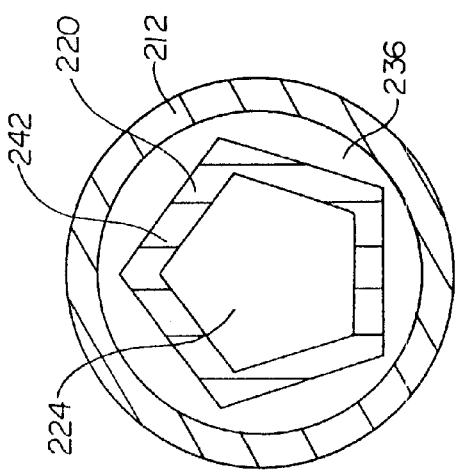
FIG. 11 is a radial cross-sectional view of the tubular shaft of the endoscopic instrument of FIG. 6 across line 7—7, according to an alternate embodiment of the present invention.

FIG. 11 depicts an alternate cross-section along line 7—7 of FIG. 6, in which a tubular shaft 212 provides both an outer wall with a non-circular cross-sectional shape and an inner wall with a non-circular cross-sectional shape for backlash reduction with a circular control member 220. This endoscopic instrument shaft reduces backlash both with regard to the movement of the entire endoscopic instrument within a working channel, as described with regard to FIG. 4, showing endoscopic instrument 106 within working channel 168, and further with regard to operation of distal end effector assembly by means of control member 220. As shown in FIGS. 2b and 4, the outer wall of the endoscopic instrument shaft 106 will contact the inner wall of working channel 168 at corners 30b.

The polygonal cross-sectional shape may be provided to the tubular shaft 212 via a mandrel or core wire with complementary ridges, around which the tubular shaft could be placed covered with heat shrink tubing, and heated. Alternatively, the cross-sectional shape may be formed by extrusion of tubular shaft 212 through a complementary die in order to achieve a polygonal cross-sectional shape within the lumen of the instrument tubular shaft.

In each of the alternate embodiments, the instrument's tubular shaft or control member is adapted to provide reduced end effector assembly backlash, while maintaining adequate fluid flow in the tubular shaft around the control member, and minimal contact between the control member and the tubular shaft inner wall. In each alternate embodiment, the non-circular cross-sectional shape of the tubular shaft lumen or control member may extend the entire length of the instrument or a portion thereof.

There have been described and illustrated herein several embodiments of an endoscope and endoscopic instrument system having reduced backlash when moving the control member within the shaft lumen of the endoscopic instrument. While particular embodiments of the invention have been described, it is not intended that the invention be limited thereto, as it is intended that the invention be as broad in scope as the art will allow and that the specification be read likewise. Thus, while a particular injection endoscopic instrument has been disclosed, it will be appreciated that endoscopic instruments having other end effectors (e.g., forceps, scissors, punches, alternate needles, etc.) can be provided with the non-circular cross-section of the invention as well. Furthermore, while a PTFE has been disclosed for the instrument's tubular shaft and control member, other low-friction materials can be used as well. Also, while a particular number of ridges and ribs have been disclosed, it will be appreciated that other numbers of ridges and ribs can be used. Alternatively, one or more spiral ridges or ribs can be provided. Furthermore, projections other than ridges can be used. Moreover, other polygonal shapes may be used for the core member and tubular shaft lumen. Also, the control member tube and the instrument shaft tube may be substituted with another tubular member having a non-circular cross-section. It will, therefore, be appreciated by those skilled in the art that yet other modifications could be made to the provided invention without deviating from its spirit and scope as so claimed.

What is claimed is:

1. An endoscopic instrument system, comprising:
   an endoscope having an elongate flexible distal portion and a proximal handle portion for manipulating said distal portion including an optics channel which receives an imaging means and a working channel having an interior surface and adapted to receive an endoscopic instrument therethrough; and
   an endoscopic instrument including an outer elongate flexible tubular member having proximal and distal ends and an inner and an outer surface, a control member having proximal and distal ends and an outer surface, said control member extending through said tubular member, an end effector assembly coupled at least to the distal end of the control member, and a first handle means for moving said control member relative to said tubular member to operate said end effector assembly coupled to the proximal end of the control member;
   wherein at least one of said inner surface of said tubular member and said outer surface of said control member is provided with a non-circular cross-sectional shape along a portion thereof adapted to reduce backlash when moving said control member relative to said tubular member of said endoscopic instrument; and
   and wherein said tubular member has an inner diameter and said control member has an outer diameter and wherein said inner diameter and said outer diameter are substantially equal to reduce backlash.

2. The endoscopic instrument of claim 1, wherein the control member further comprises an interior surface defining a lumen therethrough.

3. The endoscopic instrument of claim 1, wherein the end effector assembly comprises a needle.

4. The endoscopic instrument of claim 1, wherein the first handle means further comprises:

an internal wall defining a lumen therethrough; and a fitting adapted for attachment to a fluid source, attached to a proximal end of the first handle means.

5. The endoscopic instrument system of claim 3, further comprising a tubular shaft handle means connected to the proximal end of the outer elongate flexible tubular member.

6. The endoscopic instrument system of claim 5, wherein the first handle means further comprises a fitting adapted for attachment to a fluid source.

7. An endoscopic instrument system according to claim 1, wherein said non-circular cross-sectional shape is a polygonal shape.

8. An endoscopic instrument system according to claim 1, wherein said non-circular cross-sectional shape includes a plurality of radial projections.

9. An endoscopic instrument system according to claim 1, wherein said portion is a portion along said control member on which a jacket is provided, which includes a plurality of fins, over said control member.

10. An endoscopic instrument according to claim 9, wherein said fins are radially spaced and directed radially outward.

11. An endoscopic instrument according to claim 10, wherein said fins extend radially outward approximately 0.2 mm.

12. An endoscopic instrument according to claim 10, wherein said fins extend outward approximately 0.2 mm from said outer surface of said control member.

13. An endoscopic instrument system according to claim 1, wherein said portion is a portion of said tubular member of said endoscope instrument, and said portion includes a plurality of substantially radially inwardly directed ribs.

14. An endoscopic instrument system according to claim 1, wherein said portion is a portion of said tubular shaft which is provided with an insert having said non-circular cross-sectional shape.

15. An endoscopic instrument system according to claim 1, wherein said proximal end of said control member is substantially circular in cross-sectional shape.

16. An endoscopic instrument for insertion through an endoscope having a working channel, said endoscopic instrument comprising:

an elongate flexible tubular shaft member having proximal and distal ends and an inner and an outer surface, said outer surface having a portion having a first non-circular cross-sectional shape;

a control member having proximal and distal ends and an outer surface, said control member extending through said tubular shaft member;

wherein at least one of said inner surface of said tubular shaft member and said outer surface of said control member is provided with a second non-circular cross-sectional shape along a portion thereof adapted to reduce backlash when moving said endoscopic instrument relative to said working channel of said endoscope;

and wherein said tubular shaft member has an inner diameter and said control member has an outer diameter and wherein said inner diameter and said outer diameter are substantially equal to reduce backlash;

an end effector assembly coupled to at least one of said distal ends of said tubular member and said control member; and means for moving said control member relative to said tubular member to operate said end effector assembly.

17. An endoscopic instrument according to claim 16, wherein said portion of said outer surface of said control member or said inner surface of said tubular shaft member provided with said second non-circular cross-sectional shape has a non-circular cross-sectional shape which makes a smallest radius portion of said inner surface of said tubular shaft member nearly equal to a largest radius portion of said outer surface of said control member, such that when said control member is moved longitudinally relative to said tubular shaft member, backlash is reduced.

18. An endoscopic instrument according to claim 16, wherein said second non-circular cross-sectional shape is defined by a jacket provided over said tubular member, said jacket including a plurality of longitudinal fins.

19. An endoscopic instrument according to claim 16, wherein said second non-circular cross-sectional shape is defined by a plurality of longitudinal fins extending radially outward from said tubular member.

20. An endoscopic instrument according to claim 16, wherein said second non-circular cross-sectional shape is defined by a jacket provided over said tubular shaft member, said jacket having a substantially polygonal shape.

21. An endoscopic instrument according to claim 16, wherein said second non-circular cross-sectional shape is defined by a jacket provided over said control member, said jacket having a substantially polygonal shape.

22. An endoscopic instrument according to claim 16, wherein said second non-circular cross-sectional shape is defined by a low friction jacket provided over said portion of said outer surface of said control member, said low friction jacket having said non-circular cross-sectional shape.

23. An endoscopic instrument according to claim 16, wherein said proximal end of said tubular shaft member is substantially circular in cross-sectional shape.

24. An endoscopic instrument according to claim 16, wherein said tubular shaft member is coil.

* * * * *

UNITED STATES PATENT AND TRADEMARK OFFICE
CERTIFICATE OF CORRECTION

PATENT NO. : 6,537,205 B1  Page 1 of 1
DATED : March 25, 2003
INVENTOR(S) : Kevin W. Smith It is certified that error appears in the above-identified patent and that said Letters Patent is hereby corrected as shown below:

Column 6,
Lines 49 and 54, delete "comers" and insert therefor -- corners --.

Column 11,
Lines 22 and 28, delete "comers" and insert therefor -- corners --.

Column 14,
Line 52, after "is" and before "coil", insert -- a --.

Signed and Sealed this

Seventh Day of October, 2003

JAMES E. ROGAN
*Director of the United States Patent and Trademark Office*